United States Patent
Yao et al.

(10) Patent No.: US 9,139,355 B2
(45) Date of Patent: Sep. 22, 2015

(54) GLOVE PACKAGING HAVING ANTIMICROBIAL BARRIER

(71) Applicant: Medline Industries, Inc., Mundelein, IL (US)

(72) Inventors: Min Yao, Vernon Hills, IL (US); Samuel T. H. Amdur, III, Libertyville, IL (US)

(73) Assignee: Medline Industries, Inc., Mundelein, IL (US)

( * ) Notice: Subject to any disclaimer, the term of this patent is extended or adjusted under 35 U.S.C. 154(b) by 194 days.

(21) Appl. No.: 13/790,091

(22) Filed: Mar. 8, 2013

(65) Prior Publication Data
US 2013/0186787 A1 Jul. 25, 2013

Related U.S. Application Data

(63) Continuation-in-part of application No. 12/148,448, filed on Apr. 18, 2008, now abandoned.

(51) Int. Cl.
*B65D 85/18* (2006.01)
*A61B 19/04* (2006.01)
*B65D 83/08* (2006.01)
*B65D 81/28* (2006.01)
*A61B 17/00* (2006.01)

(52) U.S. Cl.
CPC ............. *B65D 85/18* (2013.01); *A61B 19/045* (2013.01); *B65D 83/0805* (2013.01); *A61B 2017/00889* (2013.01); *B65D 81/28* (2013.01)

(58) Field of Classification Search
CPC .... B65D 85/18; B65D 83/0805; B65D 81/28; A64B 19/045; A61B 2017/00889
USPC ................ 206/233, 216, 278, 449, 494, 438; 211/63; 229/120.01, 120.11, 242, 229/125.12; 428/357, 411.1, 704
See application file for complete search history.

(56) References Cited

U.S. PATENT DOCUMENTS

| | | |
|---|---|---|
| 3,145,840 A | 8/1964 | Wright |
| 3,239,097 A | 3/1966 | Bates et al. |
| 3,502,244 A | 3/1970 | Irvin |

(Continued)

FOREIGN PATENT DOCUMENTS

| | | |
|---|---|---|
| WO | 2005/082142 | 9/2005 |
| WO | 2007/004562 A1 | 1/2007 |

(Continued)

OTHER PUBLICATIONS

Extended European Search Report corresponding to co-pending European Patent Application Serial No. 14158296.5, European Patent Office, dated Jul. 4, 2014; (12 pages).

*Primary Examiner* — Luan K Bui
*Assistant Examiner* — Chun Cheung
(74) *Attorney, Agent, or Firm* — Nixon Peabody LLP

(57) ABSTRACT

A glove packaging comprises a container for holding the gloves and a barrier positioned to cover at least a portion of an opening in the container. The barrier protects the gloves from airborne particles and other materials or contaminants that may contaminate the gloves prior to removal from the packaging. The barrier also includes an antimicrobial material for protecting the gloves from microorganisms, pathogens or other materials or contaminants that come in contact with the barrier to further reduce the possibility of contamination.

20 Claims, 3 Drawing Sheets

(56) References Cited

U.S. PATENT DOCUMENTS

| | | | |
|---|---|---|---|
| 3,784,056 A | 1/1974 | Spruyt et al. | |
| 3,979,020 A | 9/1976 | Braber et al. | |
| 3,997,703 A | 12/1976 | Nakashio et al. | |
| 4,574,952 A | 3/1986 | Masui | |
| 4,675,347 A | 6/1987 | Mochizuki et al. | |
| 4,735,317 A | 4/1988 | Sussman et al. | |
| 4,844,293 A | 7/1989 | McLaughlin | |
| 4,863,064 A | 9/1989 | Dailey, III | |
| 4,997,105 A | 3/1991 | Fischer | |
| 5,065,863 A | 11/1991 | Moyet-Ortiz | |
| 5,357,636 A | 10/1994 | Dresdner et al. | |
| 5,379,897 A | 1/1995 | Muckenfuhs et al. | |
| 5,381,914 A | 1/1995 | Koyama et al. | |
| 5,415,320 A * | 5/1995 | North et al. | 221/63 |
| 5,501,323 A | 3/1996 | Denesha et al. | |
| 5,522,506 A * | 6/1996 | Roulin et al. | 206/531 |
| 5,542,557 A | 8/1996 | Koyama et al. | |
| 5,542,566 A | 8/1996 | Glaug et al. | |
| 5,816,440 A * | 10/1998 | Shields et al. | 221/45 |
| 5,921,434 A | 7/1999 | Hollander et al. | |
| 6,021,919 A | 2/2000 | Kelly | |
| 6,062,421 A | 5/2000 | Marley | |
| 6,112,936 A | 9/2000 | Arizmendi | |
| 6,239,097 B1 | 5/2001 | Wilson | |
| 6,514,306 B1 | 2/2003 | Rohrbach et al. | |
| 6,543,642 B1 | 4/2003 | Milliorn | |
| 6,592,702 B2 | 7/2003 | Nickell et al. | |
| 6,719,991 B2 | 4/2004 | Darouiche et al. | |
| 6,780,383 B1 | 8/2004 | Ettlinger et al. | |
| 6,782,675 B1 | 8/2004 | Banks et al. | |
| 7,189,686 B2 | 3/2007 | Burt et al. | |
| 7,238,403 B2 | 7/2007 | Koslow et al. | |
| 7,275,640 B2 | 10/2007 | Bourne et al. | |
| 7,291,370 B2 | 11/2007 | Gipson et al. | |
| 2002/0043537 A1 | 4/2002 | Serbiak | |
| 2002/0051754 A1 | 5/2002 | Schroeder et al. | |
| 2002/0179627 A1 | 12/2002 | Huang et al. | |
| 2002/0197425 A1 | 12/2002 | Wolf et al. | |
| 2004/0028931 A1 * | 2/2004 | Bletsos et al. | 428/500 |
| 2004/0043167 A1 * | 3/2004 | Holzem et al. | 428/34.9 |
| 2004/0084378 A1 | 5/2004 | Koslow | |
| 2004/0091678 A1 | 5/2004 | Jordan | |
| 2004/0166094 A1 | 8/2004 | Darouiche et al. | |
| 2004/0166102 A1 | 8/2004 | Darouiche et al. | |
| 2004/0245269 A1 | 12/2004 | Grinberg | |
| 2005/0058673 A1 * | 3/2005 | Scholz et al. | 424/401 |
| 2005/0101993 A1 | 5/2005 | Scalzo et al. | |
| 2005/0115197 A1 * | 6/2005 | Meyers et al. | 52/782.1 |
| 2005/0129937 A1 | 6/2005 | Patton et al. | |
| 2005/0150788 A1 | 7/2005 | Feusner | |
| 2005/0186258 A1 | 8/2005 | Wang et al. | |
| 2006/0091034 A1 | 5/2006 | Scalzo et al. | |
| 2006/0091035 A1 | 5/2006 | Scalzo et al. | |
| 2006/0177489 A1 | 8/2006 | Massouda et al. | |
| 2006/0204452 A1 | 9/2006 | Velamakanni et al. | |
| 2006/0222845 A1 * | 10/2006 | Deng et al. | 428/336 |
| 2007/0034330 A1 | 2/2007 | Frisk | |
| 2007/0131706 A1 | 6/2007 | Jordan et al. | |
| 2007/0144666 A1 | 6/2007 | Frisk et al. | |
| 2008/0054011 A1 | 3/2008 | Grimard et al. | |
| 2009/0130157 A1 | 5/2009 | Ylitalo et al. | |

FOREIGN PATENT DOCUMENTS

| | | |
|---|---|---|
| WO | 2007/070573 | 6/2007 |
| WO | 2008/136721 | 11/2008 |
| WO | 2009/129182 A1 | 10/2009 |

* cited by examiner

GLOVE PACKAGING HAVING ANTIMICROBIAL BARRIER

CLAIM OF PRIORITY AND CROSS-REFERENCE TO RELATED APPLICATION

This application is a Continuation-in-Part of U.S. patent application Ser. No. 12/148,448, which was filed on Apr. 18, 2008, and is incorporated herein by reference in its entirety.

TECHNICAL FIELD

The present disclosure relates generally to packaging for gloves. More particularly, the present disclosure relates to packaging for gloves having a barrier for protecting the gloves from contamination from microorganisms and other undesirable materials or contaminants, and methods for making the packaging.

BACKGROUND

Gloves are widely used as a protective measure and have become mandatory in many industries and nearly all medical and surgical settings. In particular, disposable gloves are required as a means for protecting medical and surgical staff from coming into contact with bodily fluids during surgical procedures, medical examinations, laboratory testing and other medical procedures. Disposable gloves have traditionally been made of rubber materials such as latex, thermoplastic materials such as vinyl, and other natural and synthetic materials.

Many gloves are provided in packaging having a cavity for holding the gloves. The packaging includes an opening for removing the gloves from the packaging. The opening is typically revealed by removing a perforated portion of the packaging to access the gloves. Once the perforated portion of the packaging is removed to reveal the opening, the gloves are exposed to the ambient environment. As the ambient environment may contain microorganisms, pathogens, small airborne particles of dust and debris and other air contaminants, the gloves contained in the packaging may be exposed to undesirable materials or contaminants that may contaminate the gloves while they are in the packaging.

Thus, there exists a need for a glove packaging that includes a barrier to protect gloves contained within the glove packaging from microorganisms, airborne particles and other materials or contaminants that may contaminate the gloves prior to removal from the packaging. Preferably, the barrier can also destroy any microorganisms, pathogens or other materials or contaminants that come in contact with the barrier to further reduce the possibility of contamination.

SUMMARY

According to one embodiment of the present concepts, a packaging for gloves comprises a container having a cavity for holding the gloves. The container includes an opening for removing the gloves from the container. The packaging also comprises a barrier including an antimicrobial material positioned to cover at least a portion of the opening of the container.

In another embodiment of the present concepts, a method for making a packaging for gloves comprises providing a container having a cavity for holding the gloves. The container includes an opening for removing the gloves from the container. The method further comprises providing at least a first barrier having an antimicrobial material and attaching the first barrier to the container such that the barrier at least partially covers a portion of the opening of the container.

In yet another embodiment of the present concepts, a container for holding a plurality of gloves comprises a body portion, an opening and an antimicrobial film covering the opening. The antimicrobial film includes an aperture to facilitate removal of the gloves from the opening of the container.

The above summary of the present concepts is not intended to represent each embodiment or every aspect of the present concepts. The detailed description and Figures will describe many of the embodiments and aspects of the present concepts.

BRIEF DESCRIPTION OF THE DRAWINGS

The foregoing and other advantages of the invention will become apparent upon reading the following detailed description and upon reference to the drawings.

Figure 1:
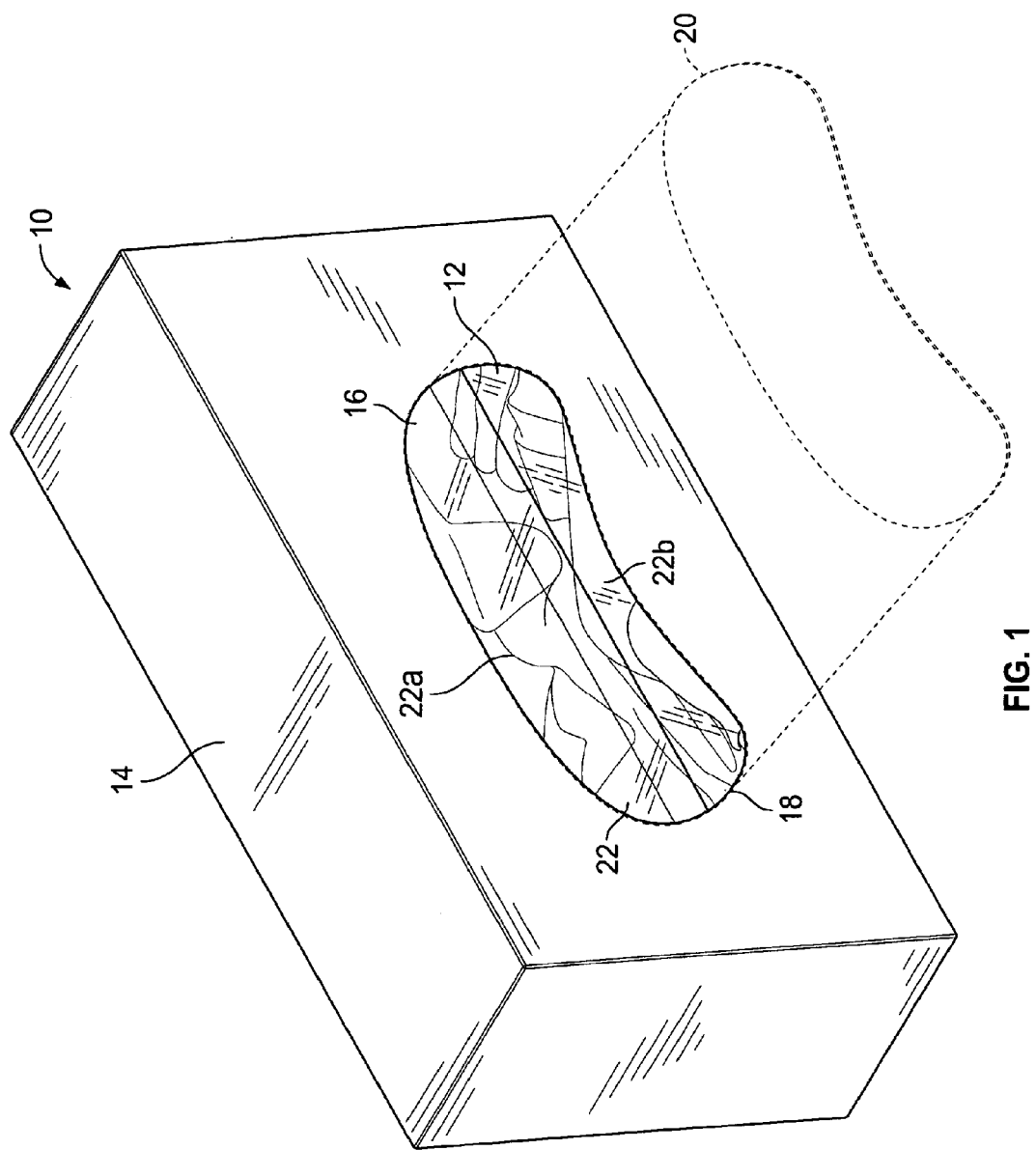
FIG. 1 is a perspective view of a glove packaging according to one embodiment of the present concepts.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

FIG. 1 illustrates a packaging 10 for gloves 12. The packaging 10 comprises a container 14 having a cavity 16 for holding the gloves 12. The container 14 includes an opening 18 for removing the gloves 12 from the container 14. The opening 18 may be in the form of different shapes, such as a circle, an oval, a square, a rectangle, or any variation of such shapes, such that a user may insert his or her hand through the opening 18 to remove one or more of the gloves 12. The opening 18 may initially be covered by a removable segment 20 that is initially formed as part of the container 14. The removable segment 20, which may be a perforated segment, is removable from the packaging 10 by a user once the packaging 10 is ready to be opened by tearing the removable segment 20 away from the packaging 10. The removable segment 20 is generally discarded after it is removed from the packaging 10. In addition to a perforated segment, the removable segment 20 may include an adhesive segment that is removable from the packaging 10.

The container 14 and removable segment 20 may be comprised of a variety of materials or combinations of materials, such as paper, plastic or fabric. The gloves 12 may include medical and/or surgical disposable gloves that are comprised of rubber materials such as latex, thermoplastic materials such as vinyl, and other natural and synthetic materials, such as nitrile, polyvinyl chloride, polyethylene, polyisoprene, neoprene, polychloriprene, etc. The gloves 12 may include other materials, such as antimicrobial coatings and/or coatings for protecting the skin that include aloe, chamomile, vitamin(s), or combinations thereof and other suitable ingredients that may provide skin care benefits, such as moisturizing and soothing dry, irritated skin. In addition to disposable gloves, it is contemplated that other types of gloves, i.e., non-medical or non-surgical gloves, could be used with the present concepts.

The packaging 10 may also comprise a barrier 22 that covers at least a portion of the opening 18 of the container 14. The barrier 22 may be a film, a piece of paper laminated with film or any type of flexible material that is suitable for providing or acting as a barrier. The barrier 22 inhibits or prevents microorganisms, pathogens, small airborne particles of dust and debris and other air contaminants from contacting and thus contaminating the gloves 12 prior to removal from the packaging 10. Thus, the barrier 22 helps to protect the gloves 12 from being exposed to undesirable materials or contaminants while the gloves 12 are in the packaging 10. Providing gloves 12 that are free from undesirable materials or contaminants reduces the risk that patients and healthcare workers will be exposed to such materials or contaminants and thereby reduces the opportunity to spread potentially harmful and infectious materials or contaminants. Furthermore, providing gloves 12 that are free from undesirable materials or contaminants also reduces or prevents cross-contamination that may occur between different patients.

In one embodiment, where the barrier 22 is a film, the film is a thin sheet of material, such as polypropylene, polystyrene, polyester, polyamide, polyvinylchloride, polyethylene (low density polyethylene, medium density polyethylene and/or high density polyethylene), polyvinylidene chloride, regenerated cellulose, cellulose acetate, and/or combinations thereof. The film material selected may be based on factors such as cost, shelf-life, barrier effectiveness, performance, etc. The film, including the paper-laminated film and any of the embodiments described herein, may have a thickness of less than about 10 mils, particularly from about 1 mil to about 6 mils. The thickness may be selected based on a variety of factors such as barrier effectiveness, cost, material(s) used, performance characteristics such as transparency and flexibility, etc. The film may be clear or colored. The film may also be printed or plain, and may be flat, patterned or embossed. Also, the film may be laminated with one or more other materials, in addition to paper, such as foil, vinyl or other materials. The film, including the paper-laminated film and any of the embodiments described herein, helps to prevent exposure of the inside of the container 14 to microorganisms, airborne particles and other materials or contaminants.

Figure 2:
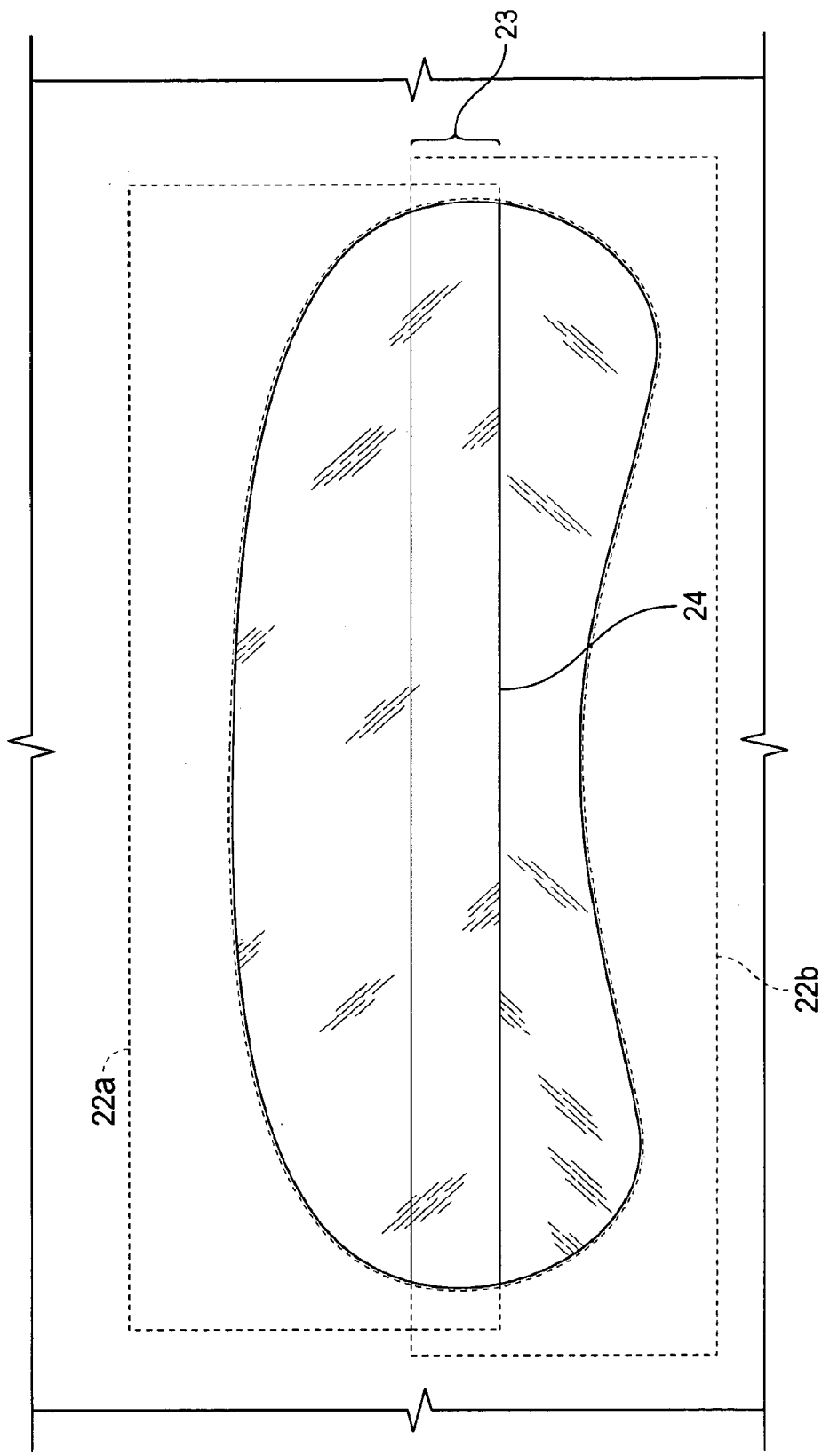
FIG. 2 is a top view of the glove packaging illustrating an antimicrobial barrier.

The barrier 22 may be a single sheet of film or may be multi-layered, as shown in FIGS. 1 and 2, as barriers 22a, 22b. The barriers 22, 22a, 22b may comprise the same type of or different materials. The barrier 22, 22a, 22b may also cover all or a portion of the top surface of the container 14, and may include an opening, aperture or slit in the middle of the barrier 22, 22a, 22b for removing the gloves 12. Having additional materials and/or additional layers may provide better protection than a single layer.

As shown in the embodiment of FIG. 2, the barriers 22a, 22b may include at least two overlapping films, including the paper-laminated film and any of the embodiments described herein, that are attached to the container 14. A first overlapping film or barrier 22a may cover a different portion of the opening 18 of the container 14 than a second overlapping film or barrier 22b. The barriers 22a, 22b may be positioned such that the barriers 22a, 22b are adjacent and overlap at an area corresponding approximately to the center of the opening 18, although it is contemplated that an overlapping portion 23 of the barriers 22a, 22b may be at other locations other than the center of the opening 18. Having the overlapping portions 23 at or near the center of the opening 18 may allow for larger areas for users to insert their hands to obtain one or more gloves 12, which may make removing the user's hand and glove easier. The overlapping portion 23 of the barriers 22a, 22b creates a slit 24 which allows a user to insert his or her hand through the slit 24 and remove a glove(s) 12 from the container 14. The barriers 22a, 22b may include a film, a piece of paper laminated with film or any type of flexible material that is suitable for providing or acting as a barrier.

Thus, one method for making the packaging 10 for gloves 12 includes providing a container 14 having a cavity 16 for holding the gloves 12 and an opening 18 for removing the gloves 12 from the container 14. Once a barrier, such as barrier 22, 22a, 22b, is provided which includes the antimicrobial material, a suitable method for attaching the barrier 22, 22a, 22b can be used to cover at least a portion of the opening 18 of the container 14. In some embodiments, the barrier 22, 22a, 22b includes overlapping films or barriers that cover the opening 18 of the container 14 and form the slit 24 for removal of the gloves 12 from the container 14.

In the embodiments shown in FIGS. 1 and 2, the barriers 22, 22a, 22b are attached to an inside surface of the top portion of the container 14. The barriers 22, 22a, 22b may be attached to the container 14 via adhesive material, glue, heat bonding, mechanical bonding, such as staples, and other suitable modes of attachment. The barriers 22, 22a, 22b may be attached along one or more peripheries, or other suitable area, of the top of the container 14. The barriers 22, 22a, 22b themselves may be made according to various methods, including extrusion, extrusion coating, co-extrusion or calendaring, or other suitable methods for making films. Extrusion, for example, is one of the most common and inexpensive methods for making a film.

The barrier 22, 22a, 22b of the embodiments described herein may include an antimicrobial material(s). The antimicrobial material(s) may include, but is/are not limited to, silver-based antimicrobial materials, copper-based antimicrobial materials, chlorhexidene gluconate, benzalkonium chloride, monoquaternary and polyquaternary ammonium salt-based antimicrobial materials (including covalent bonded quaternary ammonium salt (QAS)), biguanide-based antimicrobials such as polyhexamethylene biguanide (PHMB), triclosan, zinc pyrithione, isothiazolinone-based antimicrobials, 10,10'-oxybisphenoxarsine-based (OPBA) antimicrobials, peptide-based antimicrobials, natural antimicrobials such as hops extract, honey and chitosan-based antimicrobials, and any combinations thereof. The antimicrobial material may be selected based on a variety of factors, such as an efficacy requirement (percent of reduction), time to kill, antimicrobial spectrum, i.e., how broadly the antimicrobial material can kill bacteria, or other viruses, mold, fungi, etc. The amount of antimicrobial material used may depend on the specific antimicrobial material used, as different antimicrobial materials will require different levels for effectiveness. Thus, the amount of antimicrobial material needed will vary, but each antimicrobial material will have an antimicrobially effective level.

The antimicrobial material may be added to the barrier 22, 22a, 22b according to different methods that include, but are not limited to, spraying, coating, mixing with a polymer before extrusion, or other methods suitable to result in an application or addition of the antimicrobial material to the barrier 22, 22a, 22b. The particular method chosen may depend on the type of manufacturing process being used to make the barrier 22, 22a, 22b, the end use of the product, cost and other relevant factors. In some embodiments, spraying may be the most cost effective method. In other embodiments, the antimicrobial material may be added to the barrier 22, 22a, 22b by mixing the antimicrobial material with the barrier material before extrusion. Mixing may be advantageous as it does not require additional steps in the manufacturing process. All of these methods provide for the antimicrobial material to be included on the surface of the barrier 22, 22a, 22b, distributed within the barrier 22, 22a, 22b, or both.

Figure 3:
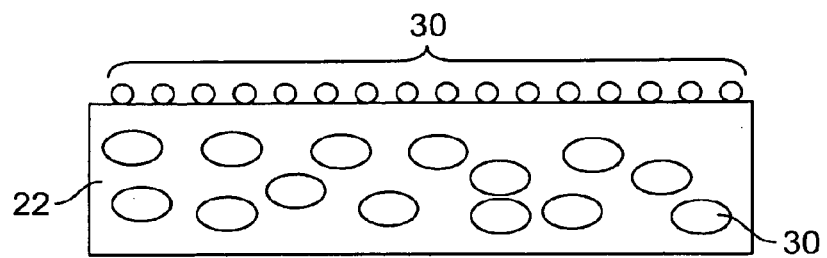
FIG. 3 is a side view of a barrier including an antimicrobial material.
Figure 4:
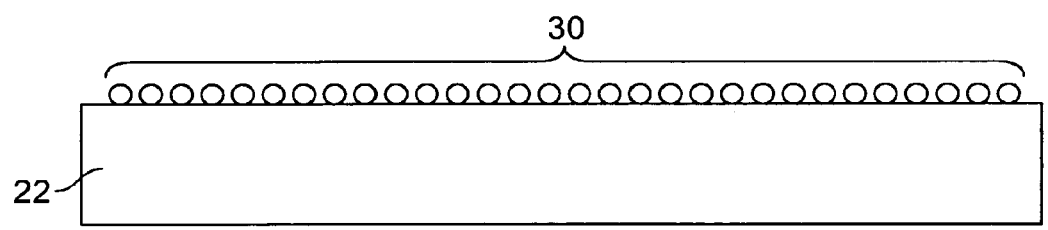
FIG. 4 is a side view of another embodiment of a barrier including an antimicrobial material.

As shown in FIG. 3, the antimicrobial material 30 may be uniformly added to the surface of and incorporated within the barrier 22, 22a, 22b such that once a microorganism comes in contact with the barrier 22, 22a, 22b, it comes into contact with the antimicrobial material 30 and is killed. While it is possible to add the antimicrobial material 30 to only a portion of the barrier 22, 22a, 22b, such as coating the surface of the barrier 22, 22a, 22b with the antimicrobial material 30 as shown in FIG. 4, it is generally more economical and effective to treat the whole barrier 22, 22a, 22b (FIG. 3). In some embodiments, the antimicrobial material 30 distributed within the barrier 22, 22a, 2b may migrate to the surface of the barrier 22, 22a, 22b once the antimicrobial material 30 on the surface is consumed.

Thus, the antimicrobial material 30 that is added to the barrier 22, 22a, 22b destroys the microorganisms and pathogens that may come in contact with the barrier 22, 22a, 22b and thus reduces and/or eliminates the amount of microorganisms that may be deposited on the disposable gloves 12 housed within the container 14. The antimicrobial material 30 in combination with the barrier 22, 22a, 22b creates a contaminant-free zone on the packaging 10 that assists in reducing or eliminating patients and healthcare workers' exposure to potentially infectious and harmful microorganisms and contaminants. Additionally, the barrier 22, 22a, 22b prevents or reduces the occurrence of airborne particles and other materials or contaminants that may contaminate the gloves prior to removal from the packaging.

In accord with aspects of the disclosed concepts, the antimicrobial material 30 can be a selected blend of two or more additives which are shown to most effectively achieve a 4-log reduction (~99.9%) of priority microorganisms and contaminants. The test inoculum with which the effectiveness of the antimicrobial material 30 is shown may comprise, singly or in any combination, *Staphylococcus aureus* (or "*S. aureus*"; a common cause of staph infection, skin infections, respiratory disease, and food poisoning), methicillin resistant *Staphylococcus aureus* (or "MRSA"), *Klebsiella pneumonia* (or "*K. pneumonia*"; a form of bacterial pneumonia), *Escherichia coli* (commonly abbreviated "*E. coli*"; a well-known cause of serious food poisoning), *Pseudomonas aeruginosa* (or "*P. aeruginosa*"; a surface-borne bacteria with potentially fatal symptoms), or *Acinetobacter baumannii* (or "*A. baumannii*"; an antibiotic-resistant pathogenic bacteria that causes pneumonia and potentially fatal infections), for example. The test procedure with which the effectiveness of the antimicrobial material 30 is shown may include International Organization for Standardization (ISO) standard 22196:2007, "Plastics—Measurement of Antibacterial Activity on Plastics Surfaces," or ISO 22196:2011, "Measurement of antibacterial activity on plastics and other non-porous surfaces," both of which are incorporated herein by reference in their entireties.

The "Value of Antimicrobial Activity" can be represented as:

$$R=[\log(B/C)]$$

where: R=value of antimicrobial activity; B=average of the number of viable cells of bacteria on the untreated test piece after 0 hours; and, C=average of the number of viable cells of bacteria on the antimicrobial test piece after 24 hours. R is commonly referred to as the "log reduction" of antimicrobial activity. It may be desirable, for some preferred embodiments, that the antimicrobial material 30 provide at least a 4-log reduction (i.e., less than approximately 0.1% survival rate) of all selected microorganisms and contaminants (e.g., those enumerated in the previous paragraph). By way of non-limiting example, some configurations may require the antimicrobial material 30 exhibit at least approximately a 4.9 log reduction of *S. aureus*, at least approximately a 4.9 log reduction of *K. pneumonia*, at least approximately a 6.0 log reduction of *E. coli*, and/or at least approximately a 5.2 log reduction of MRSA (e.g., as determined in accordance with ISO 22196:2007). For some configurations, the antimicrobial material 30 must exhibit at least approximately a 5.3 log reduction of MRSA, at least approximately a 5.1 log reduction of *K. pneumonia*, and/or at least approximately a 5.4 log reduction of *E. coli* (e.g., as determined in accordance with ISO 22196:2007). For some configurations, the antimicrobial material 30 must exhibit at least approximately a 5.6 log reduction of *P. aeruginosa* (e.g., as determined in accordance with ISO 22196:2007). Some configurations may require the antimicrobial material 30 exhibit at least approximately a 5.2 log reduction of *A. baumannii* (e.g., as determined in accordance with ISO 22196:2007).

According to some embodiments, the antimicrobial material 30 is a selected combination of zinc-based and silver-based materials which are proven, individually or in combination, to achieve the above-mentioned minimum 4-log reduction of microorganisms and contaminants. One preferred batch includes a mixture of a zinc-based antimicrobial compound, such as ULTRA-FRESH® KW-100 available from Thomson Research Associates, Inc., of Toronto, Ontario, Canada, at levels ranging from approximately 0.075% to 0.1% of the total material weight, and a silver-based antimicrobial compound, such as ULTRA-FRESH® SA-18 available from Thomson Research Associates, Inc., at levels ranging from approximately 0.1% to 0.5% of the total material weight. The silver-based antimicrobial compound may derive from the Silver Refractories chemical family, may have a specific gravity of approximately 2.7, may have a time-weighted average (TWA) of approximately 10 mg/m$^3$, may have a short term exposure limit (STEL) of 15 mg/m$^3$, and may comprise glass, oxide, and silver phosphate. In a similar regard, the zinc-based antimicrobial compound may derive from the Pyrithione chemical family, may have a specific gravity of approximately 1.8, may have a time-weighted average (TWA) of approximately 0.35 mg/m$^3$, and may comprise Bis(1-hydroxy-2(1H)-pyridinethionato-O,S)-(T-4) zinc and 2-Pyridinol-1-oxide. Optionally, the selected materials may exhibit bactericide, fungicide and/or algaecide characteristics.

As indicated above, the barrier 22 may be attached to the container 14 via an adhesive material. The adhesive may be a thermoplastic pressure sensitive adhesive (PSA), a hot-melt-adhesive, a thermoset adhesives, or any other adhesive with sufficient bonding strength for the intended application. It is desirable, for at least some applications, to pre-treat the barrier 22 prior to or during the attachment process in order to improve bonding strength and, thus, minimize any inadvertent detachment of the barrier 22 from the container 14. Applications where the barrier 22 is a polymeric film, for example, may require the contact side of the barrier, or selected portions thereof, be corona treated (also known as "air plasma" treated) to impart changes to the properties of the contact surface and thereby increase the surface tension of the film.

Alternative methods by which the surface tension of the barrier 22 may be increased include etching, priming, flame treatment, and ozone treatment. For some applications, the film surface tension (or "dyne level") is increased to at least approximately 42 dynes or, in some embodiments at least approximately 48 dynes, to assist the barrier 22 in adhering to the glove box container 14. The surface tension may be measured in accordance with DIN ISO 8296 or American Society for Testing and Materials (ASTM) standard D2578-09, both of which are incorporated herein by reference in their entireties. It may be desirable, for some embodiments, that the barrier 22 exhibits a minimum peel-force strength of 166-218 N/m or, for some embodiments, at least approximately 192 N/m. For some embodiments, the barrier 22 exhibits an average maximum pull-off force of at least approximately 184 N/m or, for some embodiments, at least approximately 230 N/m or, for some embodiments, at least approximately 275 N/m.

The container 14 of the glove packaging 10 may take on various shapes, sizes, and features within the scope of this disclosure. As shown in FIG. 1 of the drawings, for example, the container 14 is a rectangular polyhedron with opposing rectangular top and bottom walls that are interconnected by four rectangular sidewalls. The opening 18 of the glove packaging 10 is formed through the top wall of the container 14. The opening 18 may take on a variety of shapes, as indicated above; however, it may be desirable for some embodiments that the opening 18 have an elliptical shape with the major axis aligned parallel to the length of the container 14. The barrier 22 is, in at least some embodiments, a rectangular film that is adhered to the underside surface of the top wall of the container 14. For at least some embodiments, the top wall of the container is approximately 240 mm long×124 mm high (9.4 in.×4.9 in.), the film barrier is approximately 150 mm long×112 mm high (5.9 in.×4.4 in.), and/or the opening is approximately 120 mm long×60 mm high (4.7 in.×2.4 in.). Optionally, the opening can be approximately 122 mm long× 64 mm high (4.8 in.×2.5 in.). Optionally, the film barrier is approximately 160 mm wide×102mm long (6.3 in.×4.0 in.) or approximately 191 mm wide×102 mm long (7.5 in.×4.0 in.). In some embodiments, the adhesive is a thermoset Glue pattern: square parameter around the window perforation While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. A packaging for holding and dispensing gloves, the packaging comprising:
   a container with a cavity configured to hold the gloves, the container having an opening through which the gloves are removable from the container; and
   a barrier attached to the container and covering at least a portion of the opening of the container, the barrier including an antimicrobial material, the antimicrobial material including a combination of zinc-based and silver-based materials which collectively exhibit a minimum 4-log reduction of one or more predetermined pathogens, contaminants, or both,
   wherein the antimicrobial material includes approximately 0.075% to 0.1% of total weight of the zinc-based material and approximately 0.1% to 0.5% of total weight of the silver-based material.

2. The packaging of claim 1, wherein the zinc-based material has a specific gravity of approximately 1.8 and a time-weighted average (TWA) of approximately 0.35 mg/m$^3$, and the silver-based material has a specific gravity of approximately 2.7 and a time-weighted average (TWA) of approximately 10 mg/m$^3$.

3. The packaging of claim 1, wherein the antimicrobial material exhibits a minimum 4-log reduction of *Staphylococcus aureus* (*S. aureus*), methicillin resistant *Staphylococcus aureus* (MRSA), *Klebsiella pneumonia* (*K. pneumonia*), *Escherichia coli* (*E. coli*), *Pseudomonas aeruginosa*, or *Acinetobacter baumannii*, or any combinations thereof.

4. The packaging of claim 1, wherein the antimicrobial material exhibits at least approximately a 4.9 log reduction of *S. aureus*, at least approximately a 4.9 log reduction of *K. pneumonia*, at least approximately a 6.0 log reduction of *E. coli*, and at least approximately a 5.2 log reduction of MRSA.

5. The packaging of claim 1, wherein the antimicrobial material further exhibits bactericide, fungicide, or algaecide characteristics, or any combinations thereof.

6. The packaging of claim 1, wherein at least a portion of the barrier is corona treated to thereby increase the surface tension of the barrier.

7. The packaging of claim 1, wherein at least a portion of the barrier is treated to thereby increase the surface tension of the barrier to at least approximately 42 dynes.

8. The packaging of claim 1, wherein the barrier exhibits a minimum peel-force strength of at least approximately 166 N/m.

9. The packaging of claim 1, wherein the barrier exhibits an average maximum pull-off force of at least approximately 184 N/m.

10. The packaging of claim 1, wherein the barrier comprises a polymeric film.

11. The packaging of claim 10, wherein the antimicrobial material is added to the barrier by mixing the antimicrobial material with the barrier before extrusion thereof.

12. The packaging of claim 1, wherein the barrier has a thickness of from about 1 mil to about 6 mils.

13. A packaging for holding and dispensing gloves, the packaging comprising:
    a container with a cavity configured to hold the gloves, the container having an opening through which the gloves are removable from the container; and
    a barrier attached to the container and covering at least a portion of the opening of the container, the barrier including an antimicrobial material, the antimicrobial material including a combination of zinc-based and silver-based materials which collectively exhibit a minimum 4-log reduction of one or more predetermined pathogens, contaminants, or both,
    wherein the silver-based material comprises glass, oxide, and silver phosphate, and wherein the zinc-based material comprises Bis(1-hydroxy-2(1H)-pyridinethionato-O,S)-(T-4) zinc and 2-Pyridinol-1-oxide.

14. The packaging of claim 13, wherein the antimicrobial material includes approximately 0.075% to 0.1% of total weight of the zinc-based material and approximately 0.1% to 0.5% of total weight of the silver-based material.

15. The packaging of claim 13, wherein the zinc-based material has a specific gravity of approximately 1.8 and a time-weighted average (TWA) of approximately 0.35 mg/m$^3$, and the silver-based material has a specific gravity of approximately 2.7 and a time-weighted average (TWA) of approximately 10 mg/m$^3$.

16. The packaging of claim 13, wherein the antimicrobial material exhibits at least approximately a 4.9 log reduction of

*S. aureus*, at least approximately a 4.9 log reduction of *K. pneumonia*, at least approximately a 6.0 log reduction of *E. coli*, and at least approximately a 5.2 log reduction of MRSA.

17. The packaging of claim 13, wherein at least a portion of the barrier is corona treated to thereby increase the surface tension of the barrier.

18. The packaging of claim 13, wherein the barrier exhibits a minimum peel-force strength of at least approximately 166 N/m.

19. The packaging of claim 13, wherein the barrier exhibits an average maximum pull-off force of at least approximately 184 N/m.

20. A glove container for holding and dispensing a plurality of gloves, the container comprising:
    a polyhedral paper-based body portion configured to enclose therein the plurality of gloves, the body portion defining an opening through which one or more of the gloves is removable by a user; and
    a polymeric film adhered to an underside surface of a top wall of the body portion, the polymeric film covering the opening and including a slit through which one or more of the gloves is removable by the user, the polymeric film including an antimicrobial material, the antimicrobial material including approximately 0.075% to 0.1% of total weight of a zinc-based material and approximately 0.1% to 0.5% of total weight of a silver-based material.

* * * * *